(12) United States Patent
Seguin

(10) Patent No.: US 8,002,826 B2
(45) Date of Patent: ***Aug. 23, 2011

(54) ASSEMBLY FOR PLACING A PROSTHETIC VALVE IN A DUCT IN THE BODY

(75) Inventor: Jacques Seguin, Windsor (GB)

(73) Assignee: Medtronic Corevalve LLC, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/578,818

(22) Filed: Oct. 14, 2009

(65) Prior Publication Data

US 2010/0036485 A1 Feb. 11, 2010

Related U.S. Application Data

(63) Continuation of application No. 11/829,682, filed on Jul. 27, 2007, now Pat. No. 7,780,726, which is a continuation of application No. 10/482,270, filed as application No. PCT/FR02/02352 on Jul. 4, 2002, now Pat. No. 7,252,682.

(30) Foreign Application Priority Data

Jul. 4, 2001 (FR) .................................. 01 08898

(51) Int. Cl.
*A61F 2/24* (2006.01)
(52) U.S. Cl. ........................................... 623/2.17
(58) Field of Classification Search ........... 623/2.1–2.34
See application file for complete search history.

(56) References Cited

U.S. PATENT DOCUMENTS 3,657,744 A 4/1972 Ersek
(Continued)

FOREIGN PATENT DOCUMENTS

CN 2007-100074433 8/2007
(Continued)

OTHER PUBLICATIONS

Trial Transcripts, *Edwards Lifesciences AG and Edwards Lifesciences, LLC*.v. *Medtronic Core Valve LLC*, United States District Court for the District of Delaware, Civil Action No. 1:08-CV-00091-GMSM, Mar. 23, 2010-Apr. 1, 2010.

(Continued)

*Primary Examiner* — Suzette J Gherbi

(57) ABSTRACT

The present invention is an assembly comprising a prosthetic valve to be implanted; a radially expandable stent comprising at least one zone intended to be expanded to allow the stent, in the expanded state, to bear against the wall of the body duct to be fitted with the valve, this bearing making it possible to immobilize this stent with respect to this wall; and means for mounting the valve with respect to the stent, making it possible to connect the valve to the stent in such a way that the placement of the stent allows the valve to be mounted in the body duct, and expansion means such as a balloon catheter being provided to trigger expansion of the stent at the implantation site. According to the invention, the valve and the stent are designed in such a way that, at the moment when the stent is expanded, the valve is situated outside the zone or zones of the stent that are subjected to said expansion means. The invention thus consists in separating the valve and said zone or zones to be expanded, so that the expansion of the stent can be effected with an expansion force suitable for perfect anchoring of this stent in the wall of the body duct to be fitted with the valve, and without any risk of destruction or damage of the valve.

19 Claims, 4 Drawing Sheets

U.S. PATENT DOCUMENTS

| | | | |
|---|---|---|---|
| 3,671,979 A | 6/1972 | Moulopoulos | |
| 3,714,671 A | 2/1973 | Edwards et al. | |
| 3,755,823 A | 9/1973 | Hancock | |
| 3,795,246 A | 3/1974 | Sturgeon | |
| 3,839,741 A | 10/1974 | Haller | |
| 3,868,956 A | 3/1975 | Alfidi et al. | |
| 3,874,388 A | 4/1975 | King et al. | |
| 4,035,849 A | 7/1977 | Angell et al. | |
| 4,056,854 A | 11/1977 | Boretos et al. | |
| 4,183,102 A | 1/1980 | Guiset | |
| 4,222,126 A | 9/1980 | Boretos et al. | |
| 4,233,690 A | 11/1980 | Akins | |
| 4,265,694 A | 5/1981 | Boretos | |
| 4,291,420 A | 9/1981 | Reul | |
| 4,297,749 A | 11/1981 | Davis et al. | |
| 4,339,831 A | 7/1982 | Johnson | |
| 4,343,048 A | 8/1982 | Ross et al. | |
| 4,345,340 A | 8/1982 | Rosen | |
| 4,350,492 A * | 9/1982 | Wright et al. | 8/94.11 |
| 4,425,908 A | 1/1984 | Simon | |
| 4,470,157 A | 9/1984 | Love | |
| 4,501,030 A | 2/1985 | Lane | |
| 4,574,803 A | 3/1986 | Storz | |
| 4,580,568 A | 4/1986 | Gianturco | |
| 4,592,340 A | 6/1986 | Boyles | |
| 4,610,688 A | 9/1986 | Silvestrini et al. | |
| 4,612,011 A | 9/1986 | Kautzky | |
| 4,655,771 A | 4/1987 | Wallsten | |
| 4,662,885 A | 5/1987 | DiPisa, Jr. | |
| 4,665,906 A | 5/1987 | Jervis | |
| 4,681,908 A | 7/1987 | Broderick et al. | |
| 4,710,192 A | 12/1987 | Liotta et al. | |
| 4,787,899 A | 11/1988 | Lazarus | |
| 4,796,629 A | 1/1989 | Grayzel | |
| 4,797,901 A | 1/1989 | Goerne et al. | |
| 4,819,751 A | 4/1989 | Shimada et al. | |
| 4,834,755 A | 5/1989 | Silvestrini et al. | |
| 4,856,516 A | 8/1989 | Hillstead | |
| 4,872,874 A | 10/1989 | Taheri | |
| 4,878,495 A | 11/1989 | Grayzel | |
| 4,878,906 A | 11/1989 | Lindemann et al. | |
| 4,883,458 A | 11/1989 | Shiber | |
| 4,909,252 A | 3/1990 | Goldberger | |
| 4,917,102 A | 4/1990 | Miller et al. | |
| 4,922,905 A | 5/1990 | Strecker | |
| 4,954,126 A | 9/1990 | Wallsten | |
| 4,966,604 A | 10/1990 | Reiss | |
| 4,979,939 A | 12/1990 | Shiber | |
| 4,986,830 A | 1/1991 | Owens et al. | |
| 4,994,077 A | 2/1991 | Dobben | |
| 5,002,559 A | 3/1991 | Tower | |
| 5,007,896 A | 4/1991 | Shiber | |
| 5,026,366 A | 6/1991 | Leckrone | |
| 5,032,128 A | 7/1991 | Alonso | |
| 5,037,434 A | 8/1991 | Lane | |
| 5,047,041 A | 9/1991 | Samuels | |
| 5,059,177 A | 10/1991 | Towne et al. | |
| 5,061,273 A | 10/1991 | Yock | |
| 5,085,635 A | 2/1992 | Cragg | |
| 5,089,015 A | 2/1992 | Ross | |
| 5,152,771 A | 10/1992 | Sabbaghian et al. | |
| 5,161,547 A | 11/1992 | Tower | |
| 5,163,897 A | 11/1992 | Persky | |
| 5,163,953 A | 11/1992 | Vince | |
| 5,167,628 A | 12/1992 | Boyles | |
| 5,217,483 A | 6/1993 | Tower | |
| 5,232,445 A | 8/1993 | Bonzel | |
| 5,272,909 A | 12/1993 | Nguyen et al. | |
| 5,295,958 A | 3/1994 | Shturman | |
| 5,327,774 A | 7/1994 | Nguyen et al. | |
| 5,332,402 A | 7/1994 | Teitelbaum | |
| 5,350,398 A | 9/1994 | Pavcnik et al. | |
| 5,360,444 A | 11/1994 | Kusuhara | |
| 5,370,685 A * | 12/1994 | Stevens | 623/2.11 |
| 5,370,691 A * | 12/1994 | Samson | 623/1.22 |
| 5,389,106 A | 2/1995 | Tower | |
| 5,397,351 A | 3/1995 | Pavcnik et al. | |
| 5,411,552 A | 5/1995 | Andersen et al. | |
| 5,415,633 A | 5/1995 | Lazarus et al. | |
| 5,431,676 A | 7/1995 | Dubrul et al. | |
| 5,443,446 A | 8/1995 | Shturman | |
| 5,443,499 A | 8/1995 | Schmitt | |
| 5,480,424 A | 1/1996 | Cox | |
| 5,489,294 A | 2/1996 | McVenes et al. | |
| 5,489,297 A | 2/1996 | Duran | |
| 5,496,346 A | 3/1996 | Horzewski et al. | |
| 5,500,014 A | 3/1996 | Quijano et al. | |
| 5,507,767 A | 4/1996 | Maeda et al. | |
| 5,545,209 A | 8/1996 | Roberts et al. | |
| 5,545,211 A | 8/1996 | An et al. | |
| 5,545,214 A | 8/1996 | Stevens | |
| 5,554,185 A * | 9/1996 | Block et al. | 623/2.12 |
| 5,575,818 A | 11/1996 | Pinchuk | |
| 5,580,922 A | 12/1996 | Park et al. | |
| 5,591,195 A | 1/1997 | Taheri et al. | |
| 5,609,626 A | 3/1997 | Quijano et al. | |
| 5,645,559 A | 7/1997 | Hachtman et al. | |
| 5,665,115 A | 9/1997 | Cragg | |
| 5,667,523 A | 9/1997 | Bynon et al. | |
| 5,674,277 A | 10/1997 | Freitag | |
| 5,695,498 A | 12/1997 | Tower | |
| 5,702,368 A | 12/1997 | Stevens et al. | |
| 5,713,953 A | 2/1998 | Vallana et al. | |
| 5,716,417 A | 2/1998 | Girard et al. | |
| 5,746,709 A | 5/1998 | Rom et al. | |
| 5,749,890 A | 5/1998 | Shaknovich | |
| 5,766,151 A | 6/1998 | Valley et al. | |
| 5,782,809 A | 7/1998 | Umeno et al. | |
| 5,800,456 A | 9/1998 | Maeda et al. | |
| 5,800,508 A | 9/1998 | Goicoechea et al. | |
| 5,817,126 A | 10/1998 | Imran | |
| 5,824,041 A | 10/1998 | Lenker et al. | |
| 5,824,043 A | 10/1998 | Cottone, Jr. | |
| 5,824,053 A | 10/1998 | Khosravi et al. | |
| 5,824,056 A | 10/1998 | Rosenberg | |
| 5,824,061 A | 10/1998 | Quijano et al. | |
| 5,824,064 A | 10/1998 | Taheri | |
| 5,843,158 A | 12/1998 | Lenker et al. | |
| 5,851,232 A | 12/1998 | Lois | |
| 5,855,597 A | 1/1999 | Jayaraman | |
| 5,855,601 A | 1/1999 | Bessler et al. | |
| 5,861,028 A | 1/1999 | Angell | |
| 5,871,537 A | 2/1999 | Holman et al. | |
| 5,876,448 A | 3/1999 | Thompson et al. | |
| 5,888,201 A | 3/1999 | Stinson et al. | |
| 5,891,191 A | 4/1999 | Stinson | |
| 5,906,619 A | 5/1999 | Olson et al. | |
| 5,913,842 A | 6/1999 | Boyd et al. | |
| 5,925,063 A | 7/1999 | Khosravi | |
| 5,944,738 A | 8/1999 | Amplatz et al. | |
| 5,954,766 A | 9/1999 | Zadno-Azizi et al. | |
| 5,957,949 A | 9/1999 | Leonhardt et al. | |
| 5,968,068 A | 10/1999 | Dehdashtian et al. | |
| 5,980,570 A | 11/1999 | Simpson | |
| 5,984,957 A | 11/1999 | Laptewicz, Jr. et al. | |
| 5,997,573 A | 12/1999 | Quijano et al. | |
| 6,027,525 A | 2/2000 | Suh et al. | |
| 6,029,671 A | 2/2000 | Stevens et al. | |
| 6,042,589 A | 3/2000 | Marianne | |
| 6,042,598 A | 3/2000 | Tsugita et al. | |
| 6,042,607 A | 3/2000 | Williamson et al. | |
| 6,051,104 A | 4/2000 | Oriaran et al. | |
| 6,059,809 A | 5/2000 | Amor et al. | |
| 6,090,139 A | 7/2000 | Lemelson | |
| 6,110,201 A | 8/2000 | Quijano et al. | |
| 6,146,366 A | 11/2000 | Schachar | |
| 6,159,239 A | 12/2000 | Greenhalgh | |
| 6,162,208 A | 12/2000 | Hipps | |
| 6,162,245 A | 12/2000 | Jayaraman | |
| 6,171,335 B1 | 1/2001 | Wheatley et al. | |
| 6,196,996 B1 | 3/2001 | Teirstein | |
| 6,200,336 B1 | 3/2001 | Pavcnik et al. | |
| 6,203,550 B1 | 3/2001 | Olson | |
| 6,210,408 B1 | 4/2001 | Chandrasekaran et al. | |
| 6,218,662 B1 | 4/2001 | Tchakarov et al. | |
| 6,221,006 B1 | 4/2001 | Dubrul et al. | |
| 6,221,091 B1 | 4/2001 | Khosravi | |

| Patent No. | Date | Inventor(s) | Patent No. | Date | Inventor(s) |
|---|---|---|---|---|---|
| 6,241,757 B1 | 6/2001 | An et al. | 6,830,585 B1 | 12/2004 | Artof et al. |
| 6,245,102 B1 | 6/2001 | Jayaraman | 6,846,325 B2 | 1/2005 | Liddicoat |
| 6,248,116 B1 | 6/2001 | Chevilon et al. | 6,866,650 B2 | 3/2005 | Stevens et al. |
| 6,258,114 B1 | 7/2001 | Konya et al. | 6,872,223 B2 | 3/2005 | Roberts et al. |
| 6,258,115 B1 | 7/2001 | Dubrul | 6,875,212 B2 | 4/2005 | Shaolian et al. |
| 6,258,120 B1 | 7/2001 | McKenzie et al. | 6,875,231 B2 | 4/2005 | Anduiza et al. |
| 6,277,555 B1 | 8/2001 | Duran et al. | 6,883,522 B2 | 4/2005 | Spence et al. |
| 6,299,637 B1 | 10/2001 | Shaolia et al. | 6,887,266 B2 | 5/2005 | Williams et al. |
| 6,302,906 B1 | 10/2001 | Goicoechea et al. | 6,890,330 B2 | 5/2005 | Streeter et al. |
| 6,309,382 B1 | 10/2001 | Garrison et al. | 6,893,460 B2 | 5/2005 | Spenser et al. |
| 6,309,417 B1 | 10/2001 | Spence et al. | 6,896,690 B1 | 5/2005 | Lambrecht et al. |
| 6,327,772 B1 | 12/2001 | Zadno-Azizi et al. | 6,908,481 B2 | 6/2005 | Cribier |
| 6,338,735 B1 | 1/2002 | Stevens | 6,913,600 B2 | 7/2005 | Valley et al. |
| 6,348,063 B1 | 2/2002 | Yassour et al. | 6,929,653 B2 | 8/2005 | Streeter |
| 6,350,277 B1 | 2/2002 | Kocur | 6,936,057 B1 * | 8/2005 | Nobles .................... 606/194 |
| 6,352,708 B1 | 3/2002 | Duran et al. | 6,936,066 B2 | 8/2005 | Palmaz et al. |
| 6,371,970 B1 | 4/2002 | Khosravi et al. | 6,939,365 B1 | 9/2005 | Fogarty et al. |
| 6,371,983 B1 | 4/2002 | Lane | 6,951,571 B1 | 10/2005 | Srivastava |
| 6,379,383 B1 | 4/2002 | Palmaz et al. | 6,986,742 B2 | 1/2006 | Hart et al. |
| 6,380,457 B1 | 4/2002 | Yurek et al. | 6,989,027 B2 | 1/2006 | Allen et al. |
| 6,398,807 B1 | 6/2002 | Chouinard et al. | 6,989,028 B2 | 1/2006 | Lashinski et al. |
| 6,409,750 B1 | 6/2002 | Hyodoh et al. | 6,991,649 B2 | 1/2006 | Sievers |
| 6,425,916 B1 | 7/2002 | Garrison et al. | 7,018,401 B1 | 3/2006 | Hyodoh et al. |
| 6,440,164 B1 | 8/2002 | DiMatteo et al. | 7,018,406 B2 * | 3/2006 | Seguin et al. .................... 623/2.1 |
| 6,454,799 B1 | 9/2002 | Schreck | 7,041,128 B2 | 5/2006 | McGuckin, Jr. et al. |
| 6,458,153 B1 | 10/2002 | Bailey et al. | 7,044,966 B2 | 5/2006 | Svanidze et al. |
| 6,461,382 B1 | 10/2002 | Cao | 7,048,014 B2 | 5/2006 | Hyodoh et al. |
| 6,468,303 B1 | 10/2002 | Amplatz et al. | 7,097,659 B2 | 8/2006 | Woolfson et al. |
| 6,475,239 B1 | 11/2002 | Campbell et al. | 7,101,396 B2 | 9/2006 | Artof et al. |
| 6,482,228 B1 | 11/2002 | Norred | 7,105,016 B2 | 9/2006 | Shiu et al. |
| 6,488,704 B1 | 12/2002 | Connelly et al. | 7,115,141 B2 | 10/2006 | Menz et al. |
| 6,494,909 B2 | 12/2002 | Greenhalgh | 7,147,663 B1 | 12/2006 | Berg et al. |
| 6,503,272 B2 | 1/2003 | Duerig et al. | 7,153,324 B2 | 12/2006 | Case et al. |
| 6,508,833 B2 | 1/2003 | Pavcnik et al. | 7,160,319 B2 | 1/2007 | Chouinard et al. |
| 6,527,800 B1 | 3/2003 | McGuckin, Jr. et al. | 7,175,656 B2 | 2/2007 | Khairkhahan |
| 6,530,949 B2 | 3/2003 | Konya et al. | 7,186,265 B2 | 3/2007 | Sharkawy et al. |
| 6,530,952 B2 | 3/2003 | Vesely | 7,195,641 B2 | 3/2007 | Palmaz et al. |
| 6,562,031 B2 | 5/2003 | Chandrasekaran et al. | 7,198,646 B2 | 4/2007 | Figulla et al. |
| 6,562,058 B2 | 5/2003 | Seguin et al. | 7,201,761 B2 | 4/2007 | Woolfson et al. |
| 6,569,196 B1 | 5/2003 | Vesely | 7,201,772 B2 | 4/2007 | Schwammenthal et al. |
| 6,585,758 B1 | 7/2003 | Chouinard et al. | 7,252,682 B2 * | 8/2007 | Seguin .................... 623/2.17 |
| 6,592,546 B1 | 7/2003 | Barbut et al. | 7,300,457 B2 | 11/2007 | Palmaz |
| 6,605,112 B1 | 8/2003 | Moll et al. | 7,300,463 B2 | 11/2007 | Liddicoat |
| 6,613,077 B2 | 9/2003 | Gilligan et al. | 7,316,706 B2 | 1/2008 | Bloom et al. |
| 6,622,604 B1 | 9/2003 | Chouinard et al. | 7,320,704 B2 | 1/2008 | Lashinski et al. |
| 6,629,987 B1 | 10/2003 | Gambale et al. | 7,329,278 B2 * | 2/2008 | Seguin et al. .................... 623/2.1 |
| 6,635,068 B1 | 10/2003 | Dubrul et al. | 7,335,218 B2 | 2/2008 | Wilson et al. |
| 6,652,571 B1 | 11/2003 | White et al. | 7,338,520 B2 | 3/2008 | Bailey et al. |
| 6,652,578 B2 | 11/2003 | Bailey et al. | 7,374,571 B2 | 5/2008 | Pease et al. |
| 6,656,213 B2 | 12/2003 | Solem | 7,381,218 B2 | 6/2008 | Schreck |
| 6,663,663 B2 | 12/2003 | Kim et al. | 7,384,411 B1 | 6/2008 | Condado |
| 6,669,724 B2 | 12/2003 | Park et al. | 7,429,269 B2 | 9/2008 | Schwammenthal et al. |
| 6,673,089 B1 | 1/2004 | Yassour et al. | 7,435,257 B2 | 10/2008 | Lashinski et al. |
| 6,673,109 B2 | 1/2004 | Cox | 7,442,204 B2 | 10/2008 | Schwammenthal et al. |
| 6,676,698 B2 | 1/2004 | McGuckin, Jr. et al. | 7,445,630 B2 | 11/2008 | Lashinski et al. |
| 6,682,558 B2 | 1/2004 | Tu et al. | 7,462,191 B2 | 12/2008 | Spenser et al. |
| 6,682,559 B2 | 1/2004 | Myers et al. | 7,470,284 B2 | 12/2008 | Lambrecht et al. |
| 6,685,739 B2 | 2/2004 | DiMatteo et al. | 7,481,838 B2 | 1/2009 | Carpentier et al. |
| 6,689,144 B2 | 2/2004 | Gerberding | 7,534,259 B2 | 5/2009 | Lashinski et al. |
| 6,689,164 B1 | 2/2004 | Seguin | 7,544,206 B2 | 6/2009 | Cohn et al. |
| 6,692,512 B2 | 2/2004 | Jang | 7,556,645 B2 | 7/2009 | Lashinski et al. |
| 6,692,513 B2 | 2/2004 | Streeter et al. | 7,556,646 B2 | 7/2009 | Yang et al. |
| 6,695,878 B2 | 2/2004 | McGuckin, Jr. et al. | 7,682,390 B2 | 3/2010 | Seguin |
| 6,702,851 B1 | 3/2004 | Chinn et al. | 7,780,726 B2 | 8/2010 | Seguin |
| 6,719,789 B2 | 4/2004 | Cox | 7,806,919 B2 | 10/2010 | Bloom et al. |
| 6,730,118 B2 | 5/2004 | Spenser et al. | 2001/0001314 A1 | 5/2001 | Davison et al. |
| 6,730,377 B2 | 5/2004 | Wang | 2001/0002445 A1 | 5/2001 | Vesely |
| 6,733,525 B2 | 5/2004 | Yang et al. | 2001/0007956 A1 | 7/2001 | Letac et al. |
| 6,736,846 B2 | 5/2004 | Cox | 2001/0010017 A1 | 7/2001 | Letac et al. |
| 6,752,828 B2 | 6/2004 | Thornton | 2001/0011189 A1 | 8/2001 | Drasler et al. |
| 6,758,855 B2 | 7/2004 | Fulton, III et al. | 2001/0021872 A1 | 9/2001 | Bailey et al. |
| 6,769,434 B2 | 8/2004 | Liddicoat et al. | 2001/0025196 A1 | 9/2001 | Chinn et al. |
| 6,786,925 B1 | 9/2004 | Schoon | 2001/0032013 A1 | 10/2001 | Marton |
| 6,790,229 B1 | 9/2004 | Berreklouw | 2001/0039450 A1 | 11/2001 | Pavcnik et al. |
| 6,792,979 B2 | 9/2004 | Konya et al. | 2001/0041928 A1 | 11/2001 | Pavcnik et al. |
| 6,797,002 B2 | 9/2004 | Spence | 2001/0044647 A1 | 11/2001 | Pinchuk et al. |
| 6,821,297 B2 | 11/2004 | Snyders | 2002/0010508 A1 | 1/2002 | Chobotov |
| 6,830,575 B2 | 12/2004 | Stenzel et al. | 2002/0029014 A1 | 3/2002 | Jayaraman |
| 6,830,584 B1 | 12/2004 | Seguin | 2002/0032480 A1 | 3/2002 | Spence et al. |

| | | | | | | |
|---|---|---|---|---|---|---|
| 2002/0032481 A1 | 3/2002 | Gabbay | | 2004/0215333 A1 | 10/2004 | Duran et al. |
| 2002/0035396 A1 | 3/2002 | Heath | | 2004/0215339 A1 | 10/2004 | Drasler et al. |
| 2002/0042650 A1 | 4/2002 | Vardi et al. | | 2004/0225353 A1 | 11/2004 | McGuckin, Jr. |
| 2002/0052651 A1 | 5/2002 | Myers et al. | | 2004/0225354 A1 | 11/2004 | Allen et al. |
| 2002/0058995 A1 | 5/2002 | Stevens | | 2004/0254636 A1 | 12/2004 | Flagle et al. |
| 2002/0072789 A1 | 6/2002 | Hackett et al. | | 2004/0260322 A1* | 12/2004 | Rudko et al. .................. 606/167 |
| 2002/0095209 A1 | 7/2002 | Zadno-Azizi et al. | | 2004/0260389 A1 | 12/2004 | Case et al. |
| 2002/0099439 A1 | 7/2002 | Schwartz et al. | | 2004/0260390 A1 | 12/2004 | Sarac et al. |
| 2002/0103533 A1 | 8/2002 | Langberg et al. | | 2004/0260394 A1 | 12/2004 | Douk et al. |
| 2002/0107565 A1 | 8/2002 | Greenhalgh | | 2004/0267357 A1 | 12/2004 | Allen et al. |
| 2002/0111674 A1 | 8/2002 | Chouinard et al. | | 2005/0010246 A1 | 1/2005 | Streeter et al. |
| 2002/0123802 A1 | 9/2002 | Snyders | | 2005/0010285 A1 | 1/2005 | Lambrecht et al. |
| 2002/0133183 A1 | 9/2002 | Lentz et al. | | 2005/0010287 A1 | 1/2005 | Macoviak et al. |
| 2002/0138138 A1 | 9/2002 | Yang | | 2005/0015112 A1 | 1/2005 | Cohn et al. |
| 2002/0151970 A1 | 10/2002 | Garrison et al. | | 2005/0027348 A1 | 2/2005 | Case et al. |
| 2002/0161392 A1 | 10/2002 | Dubrul | | 2005/0033398 A1 | 2/2005 | Seguin |
| 2002/0161394 A1 | 10/2002 | Macoviak et al. | | 2005/0043790 A1 | 2/2005 | Seguin |
| 2002/0193871 A1 | 12/2002 | Beyersdorf et al. | | 2005/0049692 A1 | 3/2005 | Numamoto et al. |
| 2003/0014104 A1 | 1/2003 | Cribier | | 2005/0049696 A1 | 3/2005 | Siess |
| 2003/0023300 A1 | 1/2003 | Bailey et al. | | 2005/0055088 A1 | 3/2005 | Liddicoat et al. |
| 2003/0023303 A1 | 1/2003 | Palmaz et al. | | 2005/0060029 A1 | 3/2005 | Le |
| 2003/0028247 A1 | 2/2003 | Cali | | 2005/0060030 A1 | 3/2005 | Lashinski et al. |
| 2003/0036791 A1 | 2/2003 | Philipp et al. | | 2005/0075584 A1 | 4/2005 | Cali |
| 2003/0040771 A1 | 2/2003 | Hyodoh et al. | | 2005/0075712 A1 | 4/2005 | Biancucci |
| 2003/0040772 A1 | 2/2003 | Hyodoh et al. | | 2005/0075717 A1 | 4/2005 | Nguyen |
| 2003/0040792 A1 | 2/2003 | Gabbay | | 2005/0075719 A1 | 4/2005 | Bergheim |
| 2003/0050694 A1 | 3/2003 | Yang et al. | | 2005/0075724 A1 | 4/2005 | Svanidze |
| 2003/0055495 A1 | 3/2003 | Pease et al. | | 2005/0075727 A1 | 4/2005 | Wheatley |
| 2003/0065386 A1 | 4/2003 | Weadock | | 2005/0075730 A1 | 4/2005 | Myers |
| 2003/0069492 A1 | 4/2003 | Abrams et al. | | 2005/0075731 A1 | 4/2005 | Artof |
| 2003/0109924 A1 | 6/2003 | Cribier | | 2005/0085841 A1 | 4/2005 | Eversull et al. |
| 2003/0125793 A1 | 7/2003 | Vesely | | 2005/0085842 A1 | 4/2005 | Eversull et al. |
| 2003/0125795 A1 | 7/2003 | Pavcnik et al. | | 2005/0085843 A1 | 4/2005 | Opolski et al. |
| 2003/0130726 A1 | 7/2003 | Thorpe et al. | | 2005/0085890 A1 | 4/2005 | Rasmussen et al. |
| 2003/0130729 A1 | 7/2003 | Paniagua et al. | | 2005/0085900 A1 | 4/2005 | Case et al. |
| 2003/0139804 A1 | 7/2003 | Hankh et al. | | 2005/0090846 A1 | 4/2005 | Pedersen et al. |
| 2003/0149475 A1 | 8/2003 | Hyodoh et al. | | 2005/0096568 A1 | 5/2005 | Kato |
| 2003/0149476 A1 | 8/2003 | Damm et al. | | 2005/0096692 A1 | 5/2005 | Linder et al. |
| 2003/0149478 A1 | 8/2003 | Figulla et al. | | 2005/0096724 A1 | 5/2005 | Stenzel et al. |
| 2003/0153974 A1 | 8/2003 | Spenser et al. | | 2005/0096734 A1 | 5/2005 | Majercak et al. |
| 2003/0181850 A1 | 9/2003 | Diamond et al. | | 2005/0096735 A1 | 5/2005 | Hojeibane et al. |
| 2003/0191519 A1 | 10/2003 | Lombardi et al. | | 2005/0096736 A1 | 5/2005 | Osse et al. |
| 2003/0199913 A1 | 10/2003 | Dubrul et al. | | 2005/0096738 A1 | 5/2005 | Cali et al. |
| 2003/0199963 A1 | 10/2003 | Tower et al. | | 2005/0107871 A1 | 5/2005 | Realyvasquez et al. |
| 2003/0199971 A1 | 10/2003 | Tower et al. | | 2005/0113910 A1 | 5/2005 | Paniagua |
| 2003/0212410 A1 | 11/2003 | Stenzel et al. | | 2005/0119688 A1 | 6/2005 | Bergheim |
| 2003/0212454 A1 | 11/2003 | Scott et al. | | 2005/0131438 A1 | 6/2005 | Cohn |
| 2003/0220684 A1 | 11/2003 | Holman et al. | | 2005/0137686 A1 | 6/2005 | Salahieh et al. |
| 2003/0225445 A1 | 12/2003 | Derus et al. | | 2005/0137688 A1 | 6/2005 | Salahieh et al. |
| 2004/0019374 A1 | 1/2004 | Hojeibane et al. | | 2005/0137692 A1 | 6/2005 | Haug |
| 2004/0034411 A1 | 2/2004 | Quijano et al. | | 2005/0137695 A1 | 6/2005 | Salahieh |
| 2004/0039436 A1 | 2/2004 | Spenser et al. | | 2005/0137701 A1 | 6/2005 | Salahieh et al. |
| 2004/0049224 A1 | 3/2004 | Buehlmann et al. | | 2005/0143809 A1 | 6/2005 | Salahieh |
| 2004/0049262 A1 | 3/2004 | Obermiller et al. | | 2005/0148997 A1 | 7/2005 | Valley et al. |
| 2004/0049266 A1 | 3/2004 | Anduiza et al. | | 2005/0149181 A1 | 7/2005 | Eberhardt |
| 2004/0082904 A1 | 4/2004 | Houde et al. | | 2005/0165477 A1 | 7/2005 | Anduiza et al. |
| 2004/0088045 A1 | 5/2004 | Cox | | 2005/0187616 A1 | 8/2005 | Realyvasquez |
| 2004/0093005 A1 | 5/2004 | Durcan | | 2005/0197695 A1 | 9/2005 | Stacchino et al. |
| 2004/0093060 A1 | 5/2004 | Seguin et al. | | 2005/0203549 A1 | 9/2005 | Realyvasquez |
| 2004/0097788 A1 | 5/2004 | Mourles et al. | | 2005/0203605 A1 | 9/2005 | Dolan |
| 2004/0098112 A1 | 5/2004 | DiMatteo et al. | | 2005/0203614 A1 | 9/2005 | Forster et al. |
| 2004/0106976 A1 | 6/2004 | Bailey et al. | | 2005/0203618 A1 | 9/2005 | Sharkawy |
| 2004/0106990 A1 | 6/2004 | Spence et al. | | 2005/0222674 A1 | 10/2005 | Paine |
| 2004/0111096 A1 | 6/2004 | Tu et al. | | 2005/0228495 A1 | 10/2005 | Macoviak |
| 2004/0116951 A1 | 6/2004 | Rosengart | | 2005/0234546 A1 | 10/2005 | Nugent |
| 2004/0117004 A1 | 6/2004 | Osborne et al. | | 2005/0240200 A1 | 10/2005 | Bergheim |
| 2004/0122468 A1 | 6/2004 | Yodfat et al. | | 2005/0240263 A1 | 10/2005 | Fogarty et al. |
| 2004/0122516 A1 | 6/2004 | Fogarty et al. | | 2005/0261759 A1 | 11/2005 | Lambrecht et al. |
| 2004/0127979 A1 | 7/2004 | Wilson | | 2005/0273160 A1 | 12/2005 | Lashinski et al. |
| 2004/0138742 A1 | 7/2004 | Myers et al. | | 2005/0283962 A1 | 12/2005 | Boudjemline |
| 2004/0138743 A1 | 7/2004 | Myers et al. | | 2006/0004439 A1 | 1/2006 | Spenser et al. |
| 2004/0153146 A1 | 8/2004 | Lashinski et al. | | 2006/0004442 A1 | 1/2006 | Spenser et al. |
| 2004/0167573 A1 | 8/2004 | Williamson | | 2006/0004469 A1 | 1/2006 | Sokel |
| 2004/0167620 A1 | 8/2004 | Ortiz et al. | | 2006/0009841 A1 | 1/2006 | McGuckin et al. |
| 2004/0186563 A1 | 9/2004 | Iobbi | | 2006/0025855 A1 | 2/2006 | Lashinski et al. |
| 2004/0193261 A1 | 9/2004 | Berreklouw | | 2006/0052867 A1 | 3/2006 | Revuelta et al. |
| 2004/0210240 A1 | 10/2004 | Saint | | 2006/0058775 A1 | 3/2006 | Stevens et al. |
| 2004/0210304 A1 | 10/2004 | Seguin et al. | | 2006/0064058 A1 | 3/2006 | Coyle |
| 2004/0210307 A1 | 10/2004 | Khairkhahan | | 2006/0089711 A1 | 4/2006 | Dolan |

| | | |
|---|---|---|
| 2006/0100685 A1 | 5/2006 | Seguin et al. |
| 2006/0116757 A1 | 6/2006 | Lashinski et al. |
| 2006/0129051 A1 | 6/2006 | Rowe et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoeffer et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0005133 A1 | 1/2007 | Lashinski et al. |
| 2007/0010878 A1 | 1/2007 | Rafiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0043435 A1 | 2/2007 | Seguin et al. |
| 2007/0051377 A1 | 3/2007 | Douk et al. |
| 2007/0073392 A1 | 3/2007 | Heyninck-Jantz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchland et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0015687 A1 | 1/2008 | Lashinski et al. |
| 2008/0021552 A1 | 1/2008 | Gabbay |
| 2008/0048656 A1 | 2/2008 | Tan |
| 2008/0065001 A1 | 3/2008 | DiNucci et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0109073 A1 | 5/2008 | Lashinski et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichou et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0200898 A1 | 8/2008 | Lashinski et al. |
| 2008/0200980 A1 | 8/2008 | Robin et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0082857 A1 | 3/2009 | Lashinski et al. |
| 2009/0088836 A1 | 4/2009 | Bishop et al. |
| 2009/0099653 A1 | 4/2009 | Suri et al. |
| 2009/0138079 A1 | 5/2009 | Tuval et al. |
| 2009/0164004 A1 | 6/2009 | Cohn |
| 2009/0164006 A1 | 6/2009 | Seguin et al. |
| 2009/0171447 A1 | 7/2009 | Von Segesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0234443 A1 | 9/2009 | Ottma et al. |
| 2009/0240264 A1 | 9/2009 | Tuval et al. |
| 2009/0240320 A1 | 9/2009 | Tuval |
| 2009/0287296 A1 | 11/2009 | Manasse |
| 2010/0004740 A1 | 1/2010 | Seguin et al. |
| 2010/0030328 A1 | 2/2010 | Seguin et al. |
| 2010/0036485 A1 | 2/2010 | Seguin |
| 2010/0069852 A1 | 3/2010 | Kelley |
| 2010/0094411 A1 | 4/2010 | Tuval et al. |
| 2010/0100167 A1 | 4/2010 | Bortlein |
| 2010/0131054 A1 | 5/2010 | Tuval et al. |
| 2010/0137979 A1 | 6/2010 | Tuval et al. |
| 2010/0145439 A1 | 6/2010 | Seguin et al. |
| 2010/0152840 A1 | 6/2010 | Seguin et al. |
| 2010/0161045 A1 | 6/2010 | Righini |
| 2010/0198346 A1 | 8/2010 | Keogh et al. |
| 2010/0234940 A1 | 9/2010 | Dolan |
| 2010/0256723 A1 | 10/2010 | Murray |

FOREIGN PATENT DOCUMENTS

| | | |
|---|---|---|
| DE | 195 32 846 | 3/1997 |
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 48 814 | 9/2000 |
| DE | 10010074 | 10/2001 |
| DE | 100 49 812 | 4/2002 |
| DE | 100 49 813 | 4/2002 |
| DE | 100 49 815 | 4/2002 |

| | | |
|---|---|---|
| EP | 0103546 | 3/1984 |
| EP | 0597967 | 12/1994 |
| EP | 0850607 | 7/1998 |
| EP | 1057459 A1 | 6/2000 |
| EP | 1057460 A1 | 6/2000 |
| EP | 1088529 | 4/2001 |
| EP | 1255510 | 11/2002 |
| EP | 0937439 B1 | 9/2003 |
| EP | 1340473 | 9/2003 |
| EP | 0819013 | 6/2004 |
| FR | 2788217 | 12/1999 |
| FR | 2815844 | 5/2000 |
| GB | 2056023 | 3/1981 |
| GB | 2433700 | 12/2007 |
| SU | 1271508 | 11/1986 |
| WO | 91/17720 | 11/1991 |
| WO | 93/01768 | 2/1993 |
| WO | 95/29640 | 11/1995 |
| WO | 98/14137 | 4/1998 |
| WO | 98/29057 | 7/1998 |
| WO | 99/33414 | 7/1999 |
| WO | 00/41652 | 7/2000 |
| WO | 00/44313 | 8/2000 |
| WO | 00/47136 | 8/2000 |
| WO | 00/47139 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 01/76510 | 10/2001 |
| WO | 02/22054 | 3/2002 |
| WO | 02/36048 | 5/2002 |
| WO | 02/41789 | 5/2002 |
| WO | 02/43620 | 6/2002 |
| WO | 02/47575 | 6/2002 |
| WO | 02/49540 | 6/2002 |
| WO | 03/003943 | 1/2003 |
| WO | 03/003949 | 1/2003 |
| WO | 03/011195 | 2/2003 |
| WO | 03/030776 | 4/2003 |
| WO | 2004/019811 | 3/2004 |
| WO | 2004/019825 | 3/2004 |
| WO | 2004/023980 | 3/2004 |
| WO | 2004/041126 | 5/2004 |
| WO | 2004/058106 | 7/2004 |
| WO | 2004/089250 | 10/2004 |
| WO | 2005/004753 | 1/2005 |
| WO | 2005/027790 | 3/2005 |
| WO | 2005/046528 | 5/2005 |
| WO | 2006/026371 | 3/2006 |
| WO | 2008/047354 | 4/2008 |
| WO | 2008/100599 | 8/2008 |
| WO | 2008/138584 | 11/2008 |
| WO | 2008/150529 | 12/2008 |
| WO | 2009/002548 | 12/2008 |
| WO | 2009/029199 | 3/2009 |
| WO | 2009/042196 | 4/2009 |
| WO | 2009/045338 | 4/2009 |
| WO | 2009/061389 | 5/2009 |
| WO | 2009/091509 | 7/2009 |
| WO | 2009/111241 | 9/2009 |

OTHER PUBLICATIONS

Affidavit of Michael D. Gadeberg, Jul. 8, 2010 (2 Pages).
Slide Deck for Plaintiff's Closing Arguments in *Edwards Lifesciences AG and Edwards Lifesciences, LLC. V. Medtronic Core Valve LLC*, United States District Court for the District of Delaware, Civil Actoin No. 1:08-CV-00091-GMS, Apr. 1, 2010 (107 pages).
Andersen, H.R. et al, "Transluminal implantation of artificial heart valves. Description of a new expandable aortic valve and initial results with implantation by catheter technique in closed chest pigs." Euro. Heart J. (1992) 13:704-708.
Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.
Bailey, "Percutaneous Expandable Prosthetic Valves," in: Topol EJ, ed. Textbook of Interventional Cardiology. vol. II. Second edition. WB Saunders, Philadelphia, 1994:1268-1276.
Block, et al., "Percutaneous Approaches to Valvular Heart Disease," Current Cardiology Reports, vol. 7 (2005) pp. 108-113.
Bonhoeffer, et al, "Percutaneous Insertion of the Pulmonary Valve," Journal of the American College of Cardiology (United States), May 15, 2002, pp. 1664-1669.
Bonhoeffer, et al, "Percutaneous Mitral Valve Dilatation with the Multi-Track System," Catheterization and Cardiovascular Interventions—Official Journal of the Society for Cardiac Angiography & Interventions (United States), Oct. 1999, pp. 178-183.
Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.
Bonhoeffer, et al, "Technique and Results of Percutaneous Mitral Valvuloplasty With the Multi-Track System," Journal of Interventional Cardiology (United States), 200, pp. 263-268.
Bonhoeffer, et al, "Transcatheter Implantation of a Bovine Valve in Pulmonary Position: A Lamb Study," Circulation (United States), Aug. 15, 2000, pp. 813-816.
Boudjemline, et al, "Images in Cardiovascular Medicine. Percutaneous Aortic Valve Replacement in Animals," Circulation (United States), Mar. 16, 2004, 109, p. e161.
Boudjemline, et al, "Is Percutaneous Implantation of a Bovine Venous Valve in the Inferior Vena Cava a Reliable Technique to Treat Chronic Venous Insufficiency Syndrome?" Medical Science Monitor— International Medical Journal of Experimental and Clinical Research (Poland), Mar. 2004, pp. BR61-BR66.
Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.
Boudjemline, et al, "Percutaneous Aortic Valve Replacement: Will We Get There?" Heart (British Cardiac Society) (England), Dec. 2001, pp. 705-706.
Boudjemline, et al, "Percutaneous Closure of a Paravalvular Mitral Regurgitation with Amplatzer and Coil Prostheses," Archives des Maladies du Coeur Et Des Vaisseaux (France), May 2002, pp. 483-486.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.
Boudjemline, et al, "Percutaneous Implantation of a Biological Valve in Aortic Position: Preliminary Results in a Sheep Study," European Heart Journal 22, Sep. 2001, p. 630.
Boudjemline, et al, "Percutaneous Implantation of a Valve in the Descending Aorta in Lambs," European Heart Journal (England), Jul. 2002, pp. 1045-1049.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline, et al, "Percutaneous Valve Insertion: A New Approach," Journal of Thoracic and Cardiovascular Surgery (United States), Mar. 2003, pp. 741-742.
Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.
Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology (Ireland), 2001, pp. 89-93.
Boudjemline, et al, "Transcatheter Reconstruction of the Right Heart," Cardiology in the Young (England), Jun. 2003, pp. 308-311.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.

Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Hanzel, et al., "Complications of percutaneous aortic valve replacement: experience with the Criber-Edwards™ percutaneous heart valve," EuroIntervention Supplements (2006), 1 (Supplement A) A3-A8.
Huber, et al., "Do Valved Stents Compromise Coronary Flow?" Eur. J. Cardiothorac. Surg. 2004;25:754-759.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. IV-375.
Khambadkone, et al, "Percutaneous Pulmonary Valve Implantation: Impact of Morphology on Case Selection," Circulation 108 (17 Supplement), Oct. 28, 2003, p. IV-642-IV-643.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Medtech Insight, "New Frontiers in Heart Valve Disease," vol. 7, No. 8 (2005).
Palacios, "Percutaneous Valve Replacement and Repair, Fiction or Reality?" Journal of American College of Cardiology, vol. 44, No. 8 (2004) pp. 1662-1663.
Pelton et al., "Medical Uses of Nitinol," Materials Science Forum vols. 327-328, pp. 63-70 (2000).
Ruiz, "Transcathether Aortic Valve Implantation and Mitral Valve Repair: State of the Art," Pediatric Cardiology, vol. 26, No. 3 (2005).
Saliba, et al, "Treatment of Obstructions of Prosthetic Conduits by Percutaneous Implantation of Stents," Archives des Maldies du Coeur et des Vaisseaux (France), 1999, pp. 591-596.
Webb, et al., "Percutaneous Aortic Valve Implantation Retrograde from the Femoral Artery," Circulation (2006), 113;842-850.
Yonga, et al, "Effect of Percutaneous Balloon Mitral Valvotomy on Pulmonary Venous Flow in Severe Mitral Stenosis," East African Medical Journal (Kenya), Jan. 1999, pp. 28-30.
Yonga, et al, "Percutaneous Balloon Mitral Valvotomy: Initial Experience in Nairobi Using a New Multi-Track Catheter System," East African Medical Journal (Kenya), Feb. 1999, pp. 71-74.
Yonga, et al, "Percutaneous Transluminal Balloon Valvuloplasty for Pulmonary Valve Stenosis: Report on Six Cases," East African Medical Journal (Kenya), Apr. 1994, pp. 232-235.
Yonga, et al, "Percutaneous Transvenous Mitral Commissurotomy in Juvenile Mitral Stenosis," East African Medical Journal (Kenya), Apr. 2003, pp. 172-174.
Commeau et al, "Percutaneous balloon dilatation of calcific aortic valve stenosis: anatomical and haemodynamic evaluation," 1988, British Heart Journal, 59:227-238.
Stassano et al., "Mid-term results of the valve-on-valve technique for bioprosthetic failure," Eur. J. Cardiothorac. Surg. 2000; 18:453-457.
Expert report of Dr. Nigel Buller, dated Jan. 12, 2009, Edwards' United Kingdom action for invalidity, Claim No. HC 08CO0934 (83 pages).
Expert report of Dr. Nigel Buller, non-confidential annex—infringement, dated Jan. 12, 2009, Edwards' United Kingdom action for invalidity, Claim No. HC 08CO0934 (12 pages).
Expert report of Dr. Rodolfo Quijano, dated Jan. 9, 2009, Edwards' United Kingdom action for invalidity, Claim No. HC 08CO0934 (18 pages).
First Expert report of Prof. David Williams, dated Jan. 12, 2009, Edwards' United Kingdom action for invalidity, Claim No. HC 08CO0934 (41 pages).
First Expert report of Prof. Martin Rothman, dated Jan. 12, 2009, Edwards Lifesciences and Cook Biotech, Edwards' United Kingdom action for invalidity, Claim No. HC 08CO0934 (64 pages).
Fourth Expert report of Prof. Martin Rothman, dated Apr. 22, 2009, Edwards Lifesciences and Cook Biotech, Edwards' United Kingdom action for invalidity, Claim No. HC 08CO0934 (10 pages).
Second Expert report of Dr. Nigel Buller, dated Feb. 25, 2009, Edwards' United Kingdom action for invalidity, Claim No. HC 08CO0934 (24 pages).
Second Expert report of Dr. Rodolfo Quijano, dated Feb. 26, 2009, Edwards' United Kingdom action for invalidity, Claim No. HC 08CO0934 (6 pages).
Second Expert report of Prof. David Williams, dated Feb. 5, 2009, Edwards' United Kingdom action for invalidity, Claim No. HC 08CO0934 (15 pages).
Second Expert report of Prof. Martin Rothman, dated Feb. 5, 2009, Edwards Lifesciences and Cook Biotech, Edwards' United Kingdom action for invalidity, Claim No. HC 08CO0934 (11 pages).
Third Expert report of Dr. Nigel Buller, dated Apr. 21, 2009, Edwards' United Kingdom action for invalidity, Claim No. HC 08CO0934 (6 pages).
Third Expert report of Dr. Rudolfo Quijano, dated Apr. 27, 2009, Edwards' United Kingdom action for invalidity, Claim No. HC 08CO0934 (3 pages).
Third Expert report of Prof. David Williams, dated Apr. 22, 2009, Edwards' United Kingdom action for invalidity, Claim No. HC 08CO0934 (9 pages).
Pavcnik et al., "Aortic and venous valve for percutaneous insertion," Min. Invas. Ther. & Allied Techol. 2000, vol. 9, pp. 287-292.
First Expert report of Dr. Nigel Person Buller (30 pages), Corevalve, Inc. v. Edwards Lifesciences AG and Edwards Lifesciences PVT, Inc., High Court of Justice—Chancery Division Patents Court, United Kingdom, Case No. HC-07-C01243.
Second Expert report of Dr. Nigel Person Buller (5 pages), Corevalve, Inc. v. Edwards Lifesciences AG and Edwards Lifesciences PVT, Inc., High Court of Justice—Chancery Division Patents Court, United Kingdom, Case No. HC-07-C01243.
Drawing by Dr. Buller (Edwards Expert) of his interpretation of the "higher stent" referred to at col. 8, lines 13-222 of Andersen EP 592410B1 (1 page), Corevalve, Inc. v. Edwards Lifesciences AG and Edwards Lifesciences PVT, Inc., High Court of Justice—Chancery Division Patents Court, United Kingdom, Case No. HC-07-C01243.
Drawing by Dr. Buller (Edwards Expert) of "higher stent" on the schematic representation of the aortic valve area set out in Figure 2 of Rothman's first expert report (1 page), Corevalve, Inc. v. Edwards Lifesciences AG and Edwards Lifesciences PVT, Inc., High Court of Justice—Chancery Division Patents Court, United Kingdom, Case No. HC-07-C01243.
First Expert report of Professor John R. Pepper (20 pages), Corevalve, Inc. v. Edwards Lifesciences AG and Edwards Lifesciences PVT, Inc., High Court of Justice—Chancery Division Patents Court, United Kingdom, Case No. HC-07-C01243.
Second Expert report of Professor John R. Pepper (3 pages), Corevalve, Inc. v. Edwards Lifesciences AG and Edwards Lifesciences PVT, Inc., High Court of Justice—Chancery Division Patents Court, United Kingdom, Case No. HC-07-C01243.
First Expert report of Dr. Anthony C. Lunn (7 pages), Corevalve, Inc. v. Edwards Lifesciences AG and Edwards Lifesciences PVT, Inc., High Court of Justice—Chancery Division Patents Court, United Kingdom, Case No. HC-07-C01243.
First Witness statement of Stanton Rowe (9 pages), Corevalve, Inc. v. Edwards Lifesciences AG and Edwards Lifesciences PVT, Inc., High Court of Justice—Chancery Division Patents Court, United Kingdom, Case No. HC-07-C01243.
Second Witness statement of Stanton Rowe (3 pages), Corevalve, Inc. v. Edwards Lifesciences AG and Edwards Lifesciences PVT, Inc., High Court of Justice—Chancery Division Patents Court, United Kingdom, Case No. HC-07-C01243.
PVT slides naming Alain Cribier, Martin Leon, Stan Rabinovich and Stanton Rowe (16 pages), Corevalve, Inc. v. Edwards Lifesciences AG and Edwards Lifesciences PVT, Inc., High Court of Justice—Chancery Division Patents Court, United Kingdom, Case No. HC-07-C01243.

Expert Rebuttal Report of Prof. Martin T. Rothman (32 pages) redacted, *Edwards v. CoreValve*, U.S. District Court, District of Delaware, Case No. 08-091, dated Jul. 29, 2009.

Expert Report of Prof. Martin T. Rothman (74 pages) redacted, *Edwards v. CoreValve*, U.S. District Court, District of Delaware, Case No. 08-091, dated Jun. 29, 2009.

First Expert report of Richard A. Hillstead (41 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.

Reply Expert report of Richard A. Hillstead (9 pages), *Corevalve, Inc. v. Edwards Lifesciences AG and Edwards Lifesciences PVT, Inc.*, High Court of Justice—Chancery Division Patents Court, United Kingdom, Case No. HC-07-C01243.

* cited by examiner

ASSEMBLY FOR PLACING A PROSTHETIC VALVE IN A DUCT IN THE BODY

CROSS REFERENCE TO RELATED APPLICATIONS

The present application is a continuation of U.S. application Ser. No. 11/829,682, filed Jul. 27, 2007, which is a continuation of U.S. application Ser. No. 10/482,270, filed Jul. 6, 2004, now U.S. Pat. No. 7,252,682, which is the U.S. national phase under §371 of International Application No. PCT/FR02/02352, filed on Jul. 4, 2002, which was published in a language other than English and which claimed priority from French Application No. 01/08898, filed on Jul. 4, 2001, the disclosures of which are hereby incorporated by reference in their entirety.

BACKGROUND OF THE INVENTION

1. Field of the Invention

The present invention relates to an assembly for placing a prosthetic valve in a lumen of the body, especially a heart valve, and in particular an aortic valve.

2. Background Art

Documents WO 91/17720, WO 98/29057 and EP 1 057 460 each describe an assembly, including the prosthetic valve to be implanted; a radially expandable framework, called a stent, which is able, in the expanded state, to bear against the wall of the body duct to be fitted with the valve, this bearing making it possible to immobilize this stent with respect to this wall; and means for fixing the valve to the stent. The placement of the stent permits mounting of the valve in the body duct, eliminating the need for an external access route and, thus, a direct surgical intervention.

However, major drawbacks of this technique are that it entails a risk of the valve being damaged by the balloon used to expand the stent, and it limits the force of expansion that can be imparted to the stent. This limitation has repercussions on the anchoring of the stent, making a displacement of said assembly possible. This limitation also has repercussions on the leaktightness of the stent in the area of the valvular ring which is particularly affected when calcified zones give the valvular ring an irregular form and/or a certain rigidity.

Another drawback of the prior art technique is that of directly joining the commissures of the valvules to the stent. The result of this is that an expansion of the stent, and thus of the valve, different than that intended may cause poor coaptation of the valvules and, consequently, defective functioning of the valve. The stent therefore has to undergo a predetermined expansion, which prevents or complicates adaptation of this stent to the anatomical variations.

In the case of implantation of an aortic valve, the prior art technique also has drawbacks in that it necessitates very exact positioning of the stent in the aorta so that the valve is located opposite the natural valvular ring, and it entails a risk of blocking the apertures of the coronary arteries that open out at the coronary ostia.

BRIEF SUMMARY OF THE INVENTION

The present invention aims to overcome these various drawbacks. The assembly of the present invention comprises a prosthetic valve to be implanted; a radially expandable framework, or stent, comprising at least one zone intended to be expanded to allow the stent, in the expanded state, to bear against the wall of the body duct to be fitted with the valve, this bearing making it possible to immobilize the stent with respect to this wall; and means for mounting the valve with respect to the stent, making it possible to connect the valve to the stent in such a way that the placement of the stent allows the valve to be mounted in the body duct, and expansion means such as a balloon catheter being provided to trigger expansion of the stent at the implantation site. According to the invention, the valve and the stent are designed in such a way that, at the moment when the stent is expanded, the valve is situated outside the zone or zones of the stent that are subjected to said expansion means. The invention thus consists in separating the valve and said zone or zones to be expanded, so that the expansion of the stent can be effected with an expansion force suitable for perfect anchoring of this stent in the wall of the body duct to be fitted with the valve, and without any risk of destruction or damage of the valve.

According to one possibility, the stent comprises a zone for mounting of the valve, which zone is distinct from the zone or zones of the stent to be expanded, and said mounting means connect the valve to this mounting zone. The expansion of the stent thus triggers the deployment of the valve.

According to another possibility, said mounting means are designed in such a way that the valve is axially movable with respect to the stent between a position of non-implantation, in which it is situated outside the zone or zones of the stent that are to be expanded, and a position of implantation, which it can reach after expansion of the stent in the body duct, in which it is immobilized axially with respect to the stent.

The valve can thus form a subassembly separate from the stent prior to placement of this stent in the body duct, and it can be placed in the stent once the latter has been implanted. Alternatively, the valve is connected to the stent before said stent is placed in the body duct to be treated, and consequently it is introduced into this duct with the stent; said mounting means then comprise means of displacement so that, once the stent has been expanded, the valve can be displaced between said position of non-implantation and said position of implantation.

Said mounting means can then comprise one or more of the following arrangements:
  fastening members such as spikes, hooks or claws that are mounted on the valve and are able to be inserted into the wall delimiting said body duct; these fastening members can be oriented radially with respect to the valve so as to be able to be inserted into said wall upon radial deployment of the valve, or they can be oriented tangentially with respect to the valve so as to be able to be inserted into said wall upon a pivoting of the valve about its axis or upon a longitudinal movement with respect to the stent;
  burstable vesicles that are filled with biological adhesive or other suitable adhesive product and are placed on the outer face of the valve, these vesicles being able to burst when the valve is brought into its position of implantation, in particular by their being crushed between the valve and the stent;
  at least one circular or helical wire or band integrated in the peripheral wall of the valve and having a shape memory, so that it keeps the valve pressed against the stent in the position of implantation of this valve;
  conduits formed in, or fixed on, the peripheral wall of the valve, and rods formed on the stent, or vice versa, these rods being able to be engaged and being able to slide through these conduits as the valve moves from its position of non-implantation to its position of implantation, it being possible to provide means such as hooks in order to immobilize these conduits with respect to these rods in said position of implantation; wires can be connected to the ends of said rods and can pass through said conduits in order to easily guide these rods in these conduits.

Preferably, the means for mounting the valve with respect to the stent are designed in such a way that, beyond a threshold of expansion of the stent, they permit a different expansion of the valve and of the stent, so that a variation in the degree of expansion of the stent has no effect on the degree of expansion of the valve.

The valve is thus not connected directly to the stent and in particular is not connected to the stent in the area of the commissures of its valvules; in the expanded position of the stent, it can have a predetermined diameter appropriate to it, independently of the diameter of the stent. After implantation, the valve thus has a configuration ensuring that it functions properly irrespective of the degree of expansion of the stent, and this expansion of the stent can be adapted to the anatomical variability encountered at the implantation site.

The stent and/or the valve can comprise one or more elements limiting the maximum diameter of expansion of the valve, in particular in the area of the commissure points of this valve. These elements can be longitudinal wires belonging to the stent, or a framework element belonging to the valve.

Preferably, the valve has a peripheral wall with a diameter not constant in the axial direction, in particular a frustoconical shape whose diameter decreases in the distal direction, and the zone of the stent intended to receive this peripheral wall of the valve has a shape corresponding to that of this peripheral wall. This peripheral wall and this zone of the stent thus define a determined position of mounting of the valve in the stent, and they ensure that the valve is held in position in the stent. The stent advantageously has a middle portion with a smaller diameter than its end portions. It can in particular have the general form of two inverted truncated cones or an hourglass shape.

In the case where the assembly according to the invention permits mounting of an aortic valve, the stent is thus at a distance from the wall of the body duct, in particular by means of a conical or hourglass shape, allowing body fluid to pass to the coronary vessels in the area of the coronary ostia. The valve has a shape corresponding to that zone of the stent in whose area it is intended to be mounted.

Advantageously, the valve has a peripheral wall; the stent has, in the distal continuation of that zone of the stent intended to receive the valve, a foldable portion; this foldable portion is movable between an extended position, in which it is situated in the distal continuation of said zone, and a folded position, in which it is placed against the inner face of the peripheral wall of the valve and traps this peripheral wall between it and said zone of the stent, and retaining means are provided for keeping this foldable portion in this folded position. The peripheral wall of the valve is thus pressed against the stent, which ensures leaktightness of the valve with respect to the stent.

According to a preferred embodiment of the invention in this case, said retaining means are formed by a wire made of a material that is rigid but has a degree of elastic flexibility, for example a metal material having an undulated form and extending over the entire circumference of said foldable portion. Preferably, the stent comprises a sheath made of an impermeable biocompatible material and at least partially covering it. This sheath forms a fixation base for the valve and at the same time a means of sealing between the stent and the wall of the body duct. The sheath can advantageously have lateral openings that can be positioned opposite the coronary ostia at the time of implantation and thus avoid any zone of stagnation or non-circulation of the blood.

Advantageously, in the case where the assembly according to the invention comprises said foldable portion, this foldable portion is formed by a continuation of said sheath, forming a sleeve beyond that zone of the stent intended to receive the valve. Perfect leaktightness is thus obtained between the valve and the stent. The stent preferably has, fixed on said sheath, at least one inflatable peripheral chamber that can be inflated in order to form a seal ensuring leaktightness between the stent and the wall of the body duct to be fitted with the valve. This leaktightness is thus guaranteed notwithstanding the possible presence of calcified portions that give a cardiac ring an irregular shape.

Advantageously in this case, the stent has two inflatable peripheral chambers placed either side of that portion of the stent intended to bear against a cardiac valvular ring. The stent can have a cylindrical portion that can bear against a cardiac valvular ring, and a distal portion connected to this cylindrical portion. This distal portion at least partially forms said zone intended to receive the peripheral wall of the valve. The advantage is that said wall of impermeable biocompatible material is situated, in the area of this portion, at a distance from the wall of the body duct, that, in the case of implantation of an aortic valve, eliminates the risk of masking the coronary ostia.

The stent can also have a frustoconical or widened proximal portion whose diameter decreases in the distal direction and able, in the case of implantation of a heart valve, to bear against the wall of the ventricle or corresponding auricle of the heart. With this proximal portion it is possible to define the position of the stent, and thus subsequently of the valve, with respect to the zone of implantation. It also helps ensure complete immobilization of the stent. The stent can also have a supplementary bearing portion connected by filiform rods to said distal portion or to said cylindrical portion, these filiform rods having lengths such that this supplementary bearing portion is positioned beyond the coronary ostia. According to an additional characteristic, the stent has hooks that are movable between a retracted position, which they occupy before expansion of the stent, and a position of deployment into which they are brought upon deployment of the stent and in which they are inserted into a wall delimiting the body duct.

The stent can also have a portion near to the valvular ring, or situated opposite or on this valular ring, and having a high radial force, that is to say a radial force able to erase the local anatomical irregularities, for example calcifications, with a view to reinforcing the leaktightness at the junction between the stent, the sheath and the wall of the treated duct. This portion can be deployed with the aid of an expansion system with a high radial force and low compliance, for example a balloon.

The above embodiments and methods of use are explained in more detail below.

BRIEF DESCRIPTION OF THE DRAWINGS/FIGURES

Figure 7:
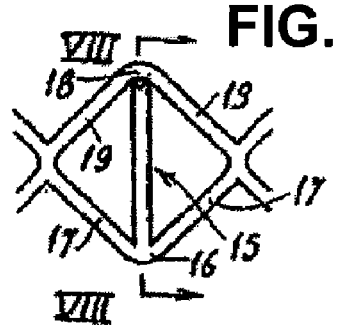
FIG. 7 is a view similar to FIG. 5, in a state of expansion of the stent.
Figure 8:
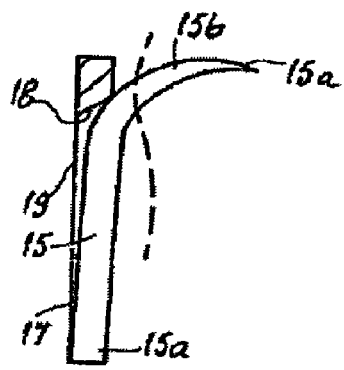
Figure 9:
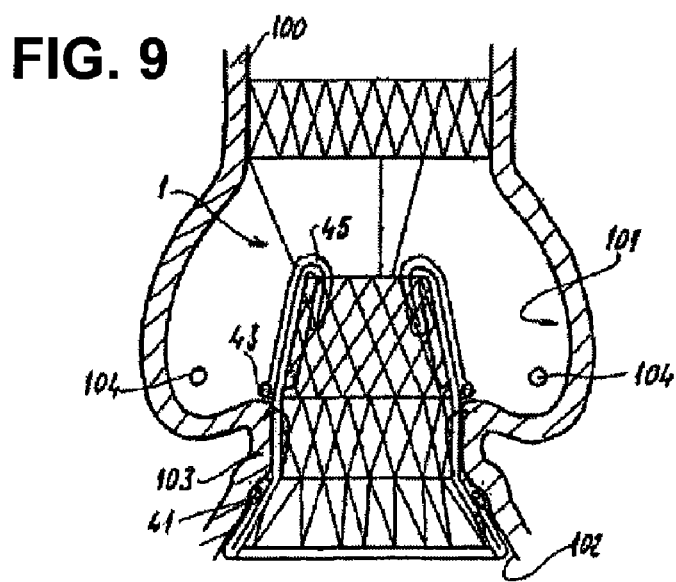
Figure 10:
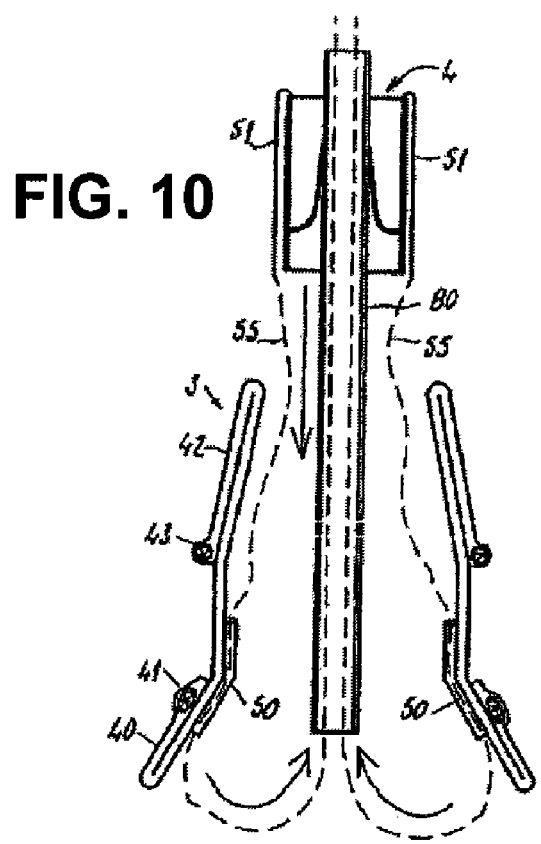
Figure 11:
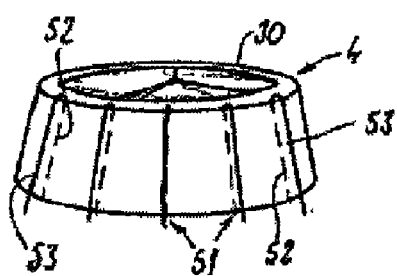
Figure 12:
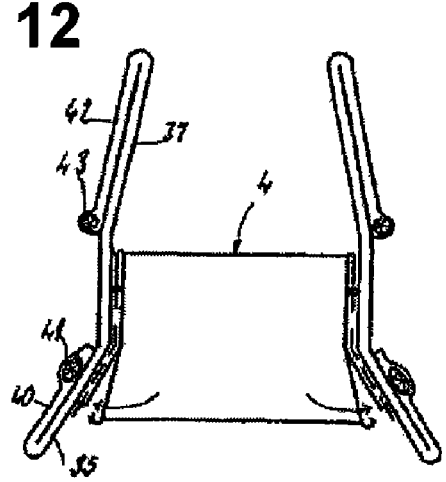
Figure 13:
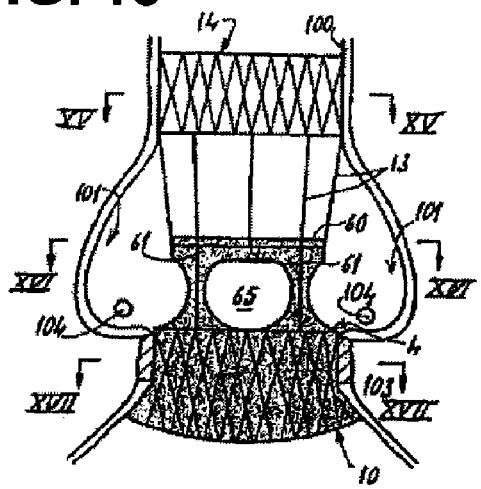
Figure 14:
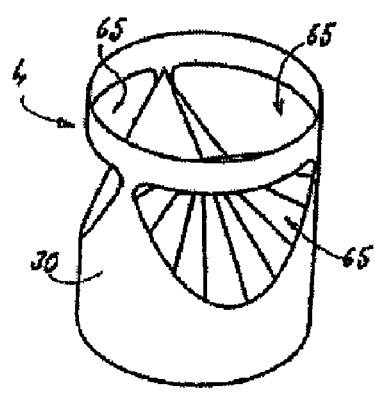
Figure 15:
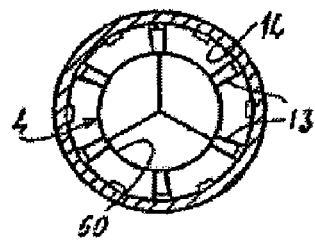
Figure 16:
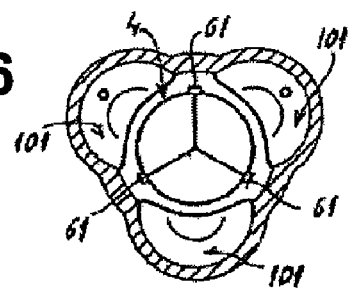
Figure 17:
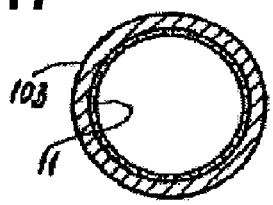

FIG. 8 and [sic] a view of the same detail, in cross section along the line VIII-VIII in FIG. 7;

FIG. 9 is a longitudinal section through the assembly according to the invention, after implantation in an aorta;

FIG. 10 is a longitudinal section through the sheath and the valve forming part of the assembly according to the invention, in a second embodiment, with the catheter used for introducing the valve into this sheath;

FIG. 11 is a perspective view of the valve according to the second embodiment;

FIG. 12 is a view similar to FIG. 10, after placement of the valve;

FIG. 13 is a view, similar to FIG. 9, of the assembly according to a third embodiment;

FIG. 14 is a perspective view of the valve that can be placed in the stent shown in FIG. 13, and FIGS. 15 through 17 are views of the assembly according to the third embodiment, in cross section on lines XV-XV, XVI-XVI and XVII-XVII, respectively, in FIG. 13.

DETAILED DESCRIPTION OF THE INVENTION

In embodiments described herein, those elements or parts that are identical or similar and are found again from one embodiment to another are designated by the same reference numbers.

Figure 1:
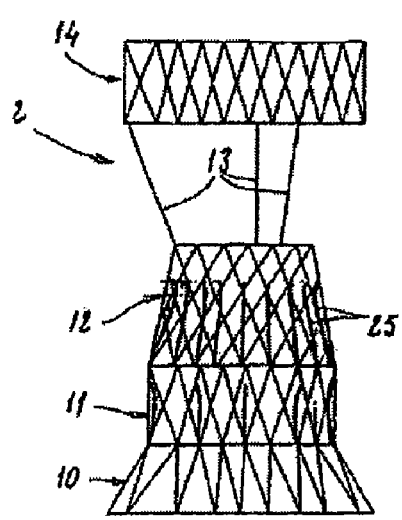
FIG. 1 is a side view of an expandable framework called a stent, which forms part of the assembly.
Figure 2:
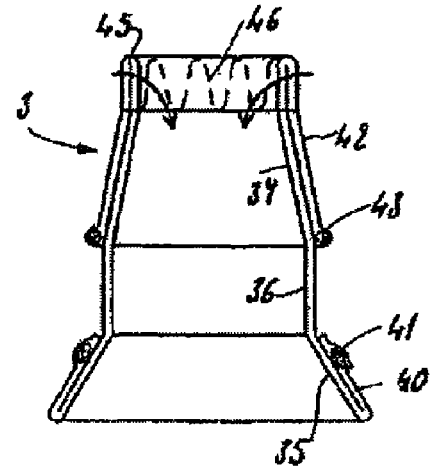
FIG. 2 is a longitudinal section through a sheath forming part of the assembly, according to a first embodiment.
Figure 3:
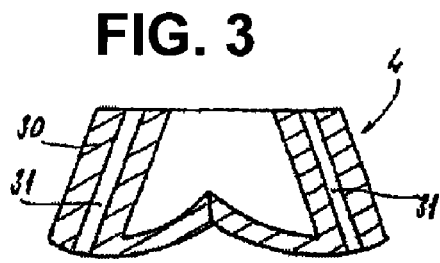
FIG. 3 is a longitudinal section through a heart valve forming part of the assembly, according to this first embodiment.

FIGS. 1 through 3 show, respectively, an expandable framework 2 called a stent, a sheath 3, and a prosthetic valve 4. This stent 2, this sheath 3 and this valve 4 form an assembly 1, which can be seen in FIG. 9, allowing the valve 4 to be placed in an aorta 100, showing the location of the coronary ostia 101 and the origin of the coronary vessels 104.

Referring to FIG. 1, it will be seen that the stent 2 comprises in succession, from one axial end to the other, in the proximal to distal direction, a frustoconical proximal portion 10, a proximal cylindrical portion 11, a distal frustoconical portion 12, several connection rods 13, and a distal cylindrical portion 14.

This stent 2 is made of a metal, steel or alloy with shape memory. This shape-memory material can in particular be the one known by the brand name Nitinol.

The portions 10 through 12 and 14 are made up of a network of filaments forming juxtaposed meshes of diamond shape or, for portion 10, of triangle shape. The material from which the stent 2 is made is such that these meshes can pass from a contracted configuration, in which the filaments are near one another, giving the meshes an elongate shape, to an expanded configuration, shown in FIG. 1 and in detail in FIG. 7, in which the filaments are spaced apart from one another.

In the contracted configuration, the assembly 1 can be introduced into the aorta 100 by means of a catheter, as far as the zone in which the prosthetic valve 4 is to be implanted; in the expanded configuration, the stent 2 bears against the aorta 100, the wall 102 of the ventricle and the natural valvular ring 103 in the manner shown in FIG. 9, such that it permits implantation of the valve 4 in place of the natural valve, the latter having been removed beforehand if necessary.

Referring to FIGS. 1 and 9, it will be seen that the portion 10 has a diameter decreasing in the distal direction, this portion 10 being configured so that, in the expanded state, it bears against the wall 102 of the ventricle of the heart.

In the expanded state, the portion 11 has a diameter such that it is able to bear against the natural valvular ring 103 and a radial force such that it can push the natural valve (or its remnants after partial exeresis) against the ring 103 in order to ensure leaktightness at this site. This portion 11 has deployable hooks 15, shown more particularly in FIGS. 5 through 8. These hooks 15 permit anchoring of the stent 2 in the aorta 100 via the sheath 3.

Figure 5:
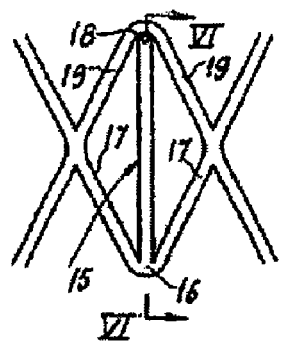
FIG. 5 is a view of another detail of the stent, on an enlarged scale, in a state of non-expansion of the stent.
Figure 6:
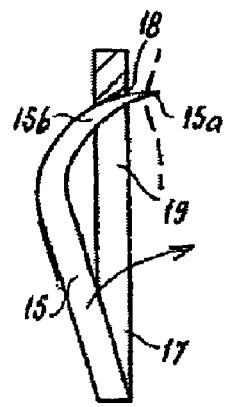
FIG. 6 is a view of the same detail, in cross section along the line VI-VI in FIG. 5.

As is shown in FIGS. 5 and 6, each hook 15 extends in the longitudinal direction of a mesh, being connected in a pivotable manner to a proximal zone 16 of connection of two proximal filaments 17. This hook 15 has a curved and tapered free end 15a, and a face 15b directed to the inside of the stent 2 and of rounded shape. The distal zone 18 of connection of the two other filaments 19 that is situated opposite the base of the hook 15 is able to bear, during expansion of the stent 2, on this face 15b, as will be inferred from comparison of FIGS. 6 and 8. The fact that this zone 18 bears along this face 15b makes it possible to deploy the hook 15 radially outward of the stent 2 and maintain this hook 15 in the deployed position in which its tapered end 15a is inserted into the wall of the ring 103. The hooks can have a fishhook shape in order to prevent their removal.

The portion 12 is directly connected to the portion 11 and has a diameter decreasing in the distal direction. This portion 12 is intended to extend to the area of the coronary ostia 101 and to receive the valve 4. Its frustoconical shape means it is possible to keep the sheath 3 at a distance from the coronary ostia 101 and thus prevent any risk of covering the apertures 104 of the coronary vessels that open out in these.

Figure 4:
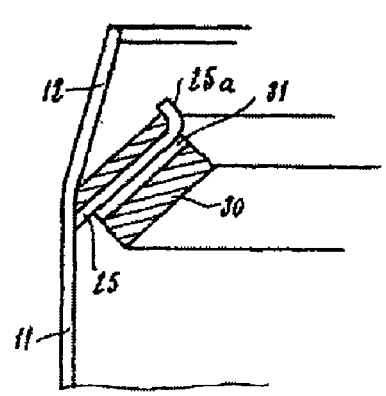
FIG. 4 is view of a detail of the stent, on an enlarged scale.

The portion 12 additionally comprises a series of internal arms 25, shown more particularly in FIG. 4. Each arm 25 is connected via its proximal end to a junction zone 16 of two proximal filaments 17 of a mesh, in proximity to the portion 11, and has a curved distal end 25a. These arms 25 are inclined toward the inside of the portion 12 before placement of the valve 4 on the stent 2, and FIG. 4 shows that in this position they can receive the valve 4. The latter actually comprises a peripheral wall 30 in which there are longitudinal tunnels 31 for receiving the arms 25; these can then be folded back against the wall of the portion 12, either by deformation of the material constituting the arms 25 and/or the portion 12, or by shape memory when use is made of a material with shape memory. These arms 25 thus allow the valve 4 to be mounted in the portion 12, as is shown in FIG. 9.

The connection rods 13 connect the distal edge of the portion 12 to the proximal edge of the portion 14. They are arranged uniformly on the periphery of the stent 2 and, as is shown in FIG. 9, they have a length that is sufficient to ensure that the portion 14 is placed, after implantation, beyond the coronary ostia 101. The spacing of these rods 13 can be curbed by an annular element making it possible to limit the upper diameter of the valve 4 to a predefined size.

The portion 14 for its part has, in the expanded state, a slightly greater diameter than the internal diameter of the aorta 100, and it bears against the wall of the latter once the stent 2 has been put in place. This portion 14 can be equipped with hooks 15.

The sheath 3 is made of an impermeable biocompatible material, such as pericardial tissue, material known under the name Dacron, or a polymer such as polyurethane, and it has portions 35, 36 and 37. These portions 35, 36 and 37 can be connected, respectively, to the portions 10, 11 and 12 and can closely match these portions 10 through 12 when the latter are in the expanded state. The connection between the sheath 3 and the portions 10 through 12 is formed by seams when the assembly 1 is assembled. The connection can also be effected by molding of a polymer material.

At the proximal end, the sheath 3 has a flap 40 extending on the outer face of the portion 35. This flap 40 has, near its free edge, an inflatable peripheral chamber 41. This chamber 41 can be inflated so as to form a seal ensuring leaktightness between the sheath 3 and the wall of the ventricle 102, on the proximal side of the natural valvular ring 103.

At the distal end, the sheath 3 has a flap 42 extending on the outer face of the portion 12. Near its free edge, this flap 42 comprises an inflatable peripheral chamber 43, similar to the chamber 41 and able to be inflated in the same way as the latter. This chamber 43 ensures leaktightness between the sheath 3 and the ring 103, on the distal side of the latter.

It will be seen from FIG. 2 that the flap 42 forms a distal sleeve 45 extending beyond the distal edge of the portion 12, and it is clear from FIG. 9 that this sleeve 45 can be folded back inside the portion 12. This sleeve 45 includes a metal wire 46 extending over the entire circumference, this wire 46 having an undulated shape and being elastically deformable. The deformability of this wire 46 allows the sleeve 45 to pass from its extended position shown in FIG. 2 to its folded position shown in FIG. 9, in which it is maintained by elastic return of the wire 46. In this folded position, the sleeve 45 is placed against the inner face of the peripheral wall 30 of the valve 4 and traps this wall 30 between it and said portion 12.

The valve 4 can be made of a biological material or of a synthetic material, or of a combination of these two types of materials. Its peripheral wall 30 has a frustoconical shape adapted to its tight engagement in the portion 12 when the arms 25 are folded back against this portion 12, which ensures complete immobilization of the valve 4 in the stent 2.

The assembly 1 is assembled by placing the sheath 3 on the stent 2 and placing the valve 4 on the arms 25, the stent 2 being in the contracted state. The assembly 1 is then placed in a catheter permitting its introduction into the patient's body, this catheter including one or more inflatable balloons able to deploy the portions 10, 11 and 14. This catheter is then brought into position in the aorta 100. The balloons are then inflated in order to deploy the portions 10, 11 and 14; the forced deployment of the portion 11 by the balloons ensures the deployment of the hooks 15 and triggers deployment of the portion 12, and consequently of the valve 4. The chambers 41, 43 are then inflated to ensure leaktightness of the sheath 3 with respect to the ring 103, and the sleeve 45 is folded back inside the portion 12 in order to clamp the peripheral wall 30 of the valve 4 against this portion 12.

As will be apparent from the above, the valve 4 and the stent 2 of the assembly 1 are designed in such a way that the valve 4 is situated outside the zone or zones 10, 11, 14 to be expanded. The stent 2 can be expanded with a force of expansion adapted for perfect anchoring of this stent 2 in the receiving walls 100, 102, 103, and without any risk to the valve 4. The hooks 15 ensure complete immobilization of the assembly 1 in the aorta 100, and the chambers 41, 43, and also the sleeve 45, ensure complete leaktightness of the assembly 1 with respect to the aorta 100.

In the second embodiment of the assembly 1, the valve 4 is not mounted in advance inside the stent 2 but is placed in it once the stent 2 has been expanded. As is shown in FIG. 10, the sheath 3 then has internal tubes 50 formed in such a way as to protrude inside the stent 2 once this sheath 3 is engaged on the stent 2. These tubes 50 can in particular be sewn or fixed by any other means to the sheath 3 after the latter has been placed on the stent 2.

Referring to FIG. 11, it will be seen that the peripheral wall 30 of the valve 4 has, in place of the tunnels 31, a series of pin-shaped clips 51. Each clip 51 has an inner arm 52 engaged longitudinally in the wall 30, and a rectilinear outer arm 53 extending along the outer face of the wall 30. The arms 53 terminate in curved ends and are connected to wires 55 engaged and able to slide in the tubes 50.

As is shown in FIG. 10, a catheter 80 is used to bring the valve 4 into position in the sheath 3. The valve 4 is engaged with sliding on the catheter 80, and the wires 55, after passing through the tubes 50, are engaged in the catheter 80 from the direction of the distal opening thereof and pass through this catheter 80 in order to be actuated from the outside. The valve 4 is put into place and deployed by pulling on the different wires 55 so as to engage the different arms 53 in the tubes 50. The inner arms 52 can comprise (see FIG. 12) proximal hooks that complete the deployment of the valve 4 by being fastened to the wall of the sheath 3, for example by means of inflation of a balloon.

In the third embodiment of the assembly 1 shown in FIG. 13, the stent 2 forms a median cage delimited by a ring 60 and by longitudinal wires 61, in which cage the valve 4 is tightly inserted. As is shown in FIG. 14, the valve 4 has a lateral wall 30 of tubular shape in which three lateral openings 65 are formed. These openings 65 are positioned opposite the coronary ostia 101 and permit a natural flow of blood, without risk of stagnation in the area of these coronary ostia 101.

The invention provides an assembly 1 for placing a valve 4 in a body duct 100, said assembly having the following advantages over similar assemblies in the prior art: elimination of the risk of damage to the valve 4 by the balloon or balloons used to expand the stent 2; possibility of applying a considerable force of expansion to the stent 2, that ensures the anchoring of the assembly 1; this considerable force of expansion additionally permits this anchoring by means of the deployable hooks 15; elimination of the risk of dilation of the valve 4 beyond a diameter no longer permitting its optimal functioning, in particular through loss of coaptation of the valvules; possibility of obtaining perfect leaktightness of the assembly 1 in the area of the valvular ring 103 and of the valve 4; elimination of the risk of blocking of the coronary ostia 101; and maintenance of a flow of body fluid all around said assembly 1 once the latter is implanted.

It goes without saying that the invention is not limited to the embodiment described above by way of example, and that instead it encompasses all alternative embodiments thereof coming within the scope of protection defined by the attached claims.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The claims in the instant application are different than those of the parent application or other related applications. The Applicant therefore rescinds any disclaimer of claim scope made in the parent application or any predecessor application in relation to the instant application. The Examiner is therefore advised that any such previous disclaimer and the cited references that it was made to avoid, may need to be revisited. Further, the Examiner is also reminded that any disclaimer made in the instant application should not be read into or against the parent application.

What is claimed is:

1. A prosthetic valve assembly comprising:
   an implantable prosthetic cardiac valve configured to permit blood flow in a first direction and to inhibit blood flow in a second direction opposite to the first direction; and
   a radially expandable annular support comprising a first inflatable peripheral chamber and a second inflatable peripheral chamber, wherein the first and second inflatable peripheral chambers are each configured to bear against a wall of a native body lumen when in an inflated state, and wherein the annular support has a central lumen for permitting blood flow therethrough when the annular support is in an expanded position,
   wherein the valve is mounted on the annular support, and wherein the valve assembly is configured to delivered by catheterization.

2. The assembly of claim 1, wherein the second inflatable chamber is configured to bear against the wall of the aorta proximal to a native valvular ring when in its inflated state.

3. The assembly of claim 1, wherein the first inflatable chamber is configured to bear against the wall of a ventricle proximal to a native valvular ring when in its inflated state.

4. The assembly of claim 1, wherein the first inflatable chamber is configured to bear against the native valvular ring.

5. The assembly of claim 1, wherein the second inflatable chamber is configured to bear against the native valvular ring.

6. The assembly of claim 1, wherein the annular support is formed generally in an hourglass shape.

7. The assembly of claim 1, wherein the annular support is formed at least partially of a biocompatible polymer.

8. The assembly of claim 7, wherein the first and second inflatable chambers are formed of a biocompatible polymer.

9. The assembly of claim 1, wherein the first and second inflatable chambers are configured to prevent leakage between the annular support and the native valvular ring.

10. The assembly of claim 2, wherein the second inflatable chamber is configured such that it is below the coronary ostia and does not obstruct the coronary arteries when in the inflated state.

11. The assembly of claim 1, wherein, when the annular support is in the expanded position, the valve is substantially within the native valvular ring.

12. The assembly of claim 1, wherein the annular support has a different diameter at the location of the first inflatable chamber than at the location of the second inflatable chamber when the annular support is in the expanded position.

13. The assembly of claim 12, wherein the annular support has a larger diameter at the location of the first inflatable chamber than at the location of the second inflatable chamber when the annular support is in the expanded position.

14. A prosthetic valve assembly comprising:
    a prosthetic cardiac valve configured to replace the function of a natural cardiac valve; and
    a radially expandable tubular support having a distal inflatable chamber and a proximal inflatable chamber connected thereto, wherein the distal inflatable chamber is configured to bear against a wall of an aorta in an inflated state, and wherein the proximal inflatable chamber is configured to bear against a wall of a ventricle in an inflated state,
    wherein the prosthetic cardiac valve is mounted on the tubular support, and wherein the valve assembly is configured to delivered by catheterization.

15. The assembly of claim 14, wherein the tubular support has a different diameter at the location of the proximal inflatable chamber than at the location of the distal inflatable chamber when the tubular support is in an expanded position.

16. The assembly of claim 15, wherein the tubular support has a larger diameter at the location of the proximal inflatable chamber than at the location of the distal inflatable chamber when the tubular support is in the expanded position.

17. The assembly of claim 14, wherein the distal inflatable chamber is configured such that it is below the coronary ostia and does not obstruct the coronary arteries when in the inflated state.

18. The assembly of claim 14, wherein the distal and proximal inflatable chambers are configured to prevent leakage between the tubular support and a native valvular ring.

19. The assembly of claim 14, wherein, when the tubular support is in an expanded position, the valve is substantially within a native cardiac valvular ring.

* * * * *